United States Patent [19]

Salmons et al.

[11] Patent Number: 6,117,681
[45] Date of Patent: Sep. 12, 2000

[54] PSEUDOTYPED RETROVIRAL PARTICLES

[75] Inventors: Brian Salmons, Ainhofen, Germany; Jörg G. Baumann, Vienna, Austria

[73] Assignees: Bavarian Nordic Research Inst. A/S, Glostrup; GSF-Gessellschaft fur Umwelt und Gesundheit GmbH, Neuherberg, both of Germany

[21] Appl. No.: 08/936,756

[22] Filed: Sep. 25, 1997

[30] Foreign Application Priority Data

Mar. 29, 1995 [DK] Denmark .................................. 0327/95
Mar. 27, 1996 [WO] WIPO ...................... PCT/EP96/01348

[51] Int. Cl.[7] ................................................... C12N 5/06
[52] U.S. Cl. ........................... 435/456; 435/325; 435/352
[58] Field of Search ................................ 435/325, 352, 435/353, 351, 366, 440, 456, 457, 235, 239, 320.1, 455

[56] References Cited

U.S. PATENT DOCUMENTS

| | | | |
|---|---|---|---|
| 4,861,719 | 8/1989 | Miller ...................................... | 435/236 |
| 5,278,056 | 1/1994 | Bank et al. ............................. | 435/456 |
| 5,449,614 | 9/1995 | Danos et al. ............................ | 435/457 |
| 5,658,775 | 8/1997 | Gilboa .................................... | 435/456 |

FOREIGN PATENT DOCUMENTS

| | | |
|---|---|---|
| WO 92/14829 | 9/1992 | WIPO . |
| WO 94/23048 | 10/1994 | WIPO . |
| WO 94/29440 | 12/1994 | WIPO . |
| WO 96/04934 | 2/1996 | WIPO . |
| WO 96/35454 | 11/1996 | WIPO . |

OTHER PUBLICATIONS

Emi et al. Journal of Virology. vol. 65, No. 3, pp. 1202–1207, Mar. 1991.
Burns et al. Proceedings of the National Academy of Sciences, USA. vol. 90, pp. 8033–8037, Sep. 1993.
Hopkins, N. Proceedings of the National Academy of Sciences, USA. vol. 90, pp. 8759–8760, Oct. 1993.
Schochetman et al. Virology. vol. 97, pp. 342–353, 1979.
Salmons, B. et al., "Construction of Retroviral Vectors for Targeted Delivery and Expression of Therapeutic Genes," *Leukemia*, 9, Suppl. 1:S53–S60, (1995).
Weiss, R.A., Chapter 1: "Cellular Receptors and Viral Glycoproteins Involved in Retrovirus Entry," *The Retroviridae*, vol. 2 pp. 1–54, (1993).
Günzburg, W.H. and Salmons, B., "Factors controlling the expression of mouse mammary tumour virus," *Biochem. J.*, 283:625–632 (1992).
Takeuchi, Y. et al., "Retroviral Pseudotypes Produced by Rescue of a Moloney Murine Leukemia Virus Vector by C–type, but Not D–type, Retroviruses," *Virol.*, 186:792–794, (1992).
Vile, R.G., et al., "A Murine Cell Line Producing HTLV–1 Pseudotype Virions Carrying a Selectable Marker Gene," *Virol.*, 180:420–424, (1991).

Wilson, C., et al., "Formation of Infectious Hybrid Virions with Gibbon Ape Leukemia Virus and Human T–Cell Leukemia Virus Retroviral Envelope Glycoproteins and the gag and pol Proteins of Moloney Murine Leukemia Virus," *J. Virol.*, 63(5):2374–2378, (1989).
Markowitz, D.A., et al., "A Safe Packaging Line for Gene Transfer: Separating Viral Genes on Two Different Plasmids," *J. Virol.*, 62(4):1120–1124, (1988).
Markowitz, D., et al., "Construction and Use of a Safe and Efficient Amphotropic Packaging Cell Line," *Virol.*, 167:400–406, (1988).
Emi, N., et al., "Pseudotype Formation of Retrovirus Vectors Containing the Glycoprotein of Vesicular Stomatitis Virus," *J. Cell Biochem., Suppl.* D408:367, (1990).
Yang, Y., et al., "Development and Characterization of a Packaging Cell Line that Generates Novel Retroviral Vectors with Broad Mammalian Host Cell Range," *Blood*, 82(10:Suppl. 1185):300A, (1993).
Yang, Y., et al., "Vesicular Stomatitis Virus (VSV) Pseudotyped Murine Retrovirus Mediates Gene Transfer into Human Hematopoietic Cells", *Blood*, 84:(10 Suppl. 1417):358a, (1994).
Yang, Y., et al., "Inducible, High–Level Production of Infectious Murine Leukemia Retroviral Vector Particles Pseudotyped with Vesicular Stomatitis Virus G Enevelope Protein," *Human Gene Therapy*, 6:1203–1213, (1995).
Lefkowitz, E.J., et al., "Complementation of a Vesicular Stomatitis Virus Glycoprotein G Mutant with Wild–Type Protein Expressed from either a Bovine Papilloma Virus or a Vaccinia Virus Vector System," *Virol.*, 178:373–383, (1990).
Burns, J.C., et al., "Pantropic Retroviral Vector–Mediated Gene Transfer, Integration, and Expression in Cultured Newt Limb Cells," *Develop. Biol.*, 165:285–289, (1994).
Emi, N., et al., "Pseudotype Formation of Murine Leukemia Virus with the G Protein of Vesicular Stomatitis Virus," *J. Virol.*, 65(3):1202–1207, (1991).
Rolls, M.M., et al., "Novel Infectious Particles Generated by Expression of the Vesicular Stomatitis Virus Glycoprotein from a Self–Replicating RNA," *Cell*, 79:497–506, (1994).
Yee, J.–K., et al., "Generation of High–Titer Pseudotyped Retroviral Vectors with Very Broad Host Range," *Meth. Cell Biol.*, 43:99–112, (1994).
Lin, S. et al., "Integration and Germ–Line Transmission of a Pseudotyped Retroviral Vector in Zebrafish," *Science*, 265:666–669, (1994).

(List continued on next page.)

*Primary Examiner*—Remy Yucel
*Attorney, Agent, or Firm*—Hamilton, Brook, Smith & Reynolds, P.C.

[57] ABSTRACT

The present invention relates to a retroviral vector system comprising a packaging cell line that synthesize the core and enzymatic proteins of MLV virus from one or more gag and pol containing constructs and the envelope of MMTV virus from the same or an independent env containing construct, and to pseudotyped retroviral particles produced by culturing said retroviral vector system transfected with a MLV based retroviral vector, and isolation of said pseudotyped retroviral particles.

18 Claims, 2 Drawing Sheets

OTHER PUBLICATIONS

Burns, J.C. et al., "Vesicular Stomatitis Virus G. Glycoprotein Pseudotyped Retroviral Vectors: Concentration to Very High Titer and Efficient Gene Transfer into Mammalian and Nonmammalian Cells," *Proc. Natl. Acad. Sci. USA*, 90:8033–8037 (1993).

Yee, J.–K., et al., "A General Method for the Generation of High–Titer, Pantropic Retroviral Vectors: Highly Efficient Infection of Primary Hepatocytes," *Proc. Natl. Acad. Sci. USA*, 91:9564–9568, (1994).

Miller, A.D., et al., "Use of Retroviral Vector5 for Gene Transfer and Expression," *Meth. Enzymol.*, 271:581–599, (1993).

Ory, D.S., et al., "A stable human–derived packaging cell line for production of high titer retrovirus/vesicular stomatits virus G pseudotyped," *Proc. Natl. Acad. Sci. USA*, 93:11400–11406, (1996).

PSEUDOTYPED RETROVIRAL PARTICLES

BACKGROUND OF THE INVENTION

The use of retroviral vectors (RV) for gene therapy has received much attention and currently is the method of choice for the transferral of therapeutic genes in a variety of approved protocols both in the USA and in Europe (Kotani, H., et. al., *Human Gene Therapy*, 5:19–28 (1994)). However most of these protocols require that the infection of target cells with the RV carrying the therapeutic gene occurs in vitro, and successfully infected cells are then returned to the affected individual (Rosenberg, S. A. et. al., *Human Gene Therapy*, 3:75–90 (1992); (Anderson, W. F., "Human Gene Therapy", *Science*, 256:808–813 (1992)). Such ex vivo gene therapy protocols are ideal for correction of medical conditions in which the target cell population can be easily isolated (e.g. lymphocytes). Additionally the ex vivo infection of target cells allows the administration of large quantities of concentrated virus which can be rigorously safety tested before use.

Unfortunately, only a fraction of the possible applications for gene therapy involve target cells that can be easily isolated, cultured and then reintroduced. Additionally, the complex technology and associated high costs of ex vivo gene therapy effectively preclude its disseminated use world-wide. Future facile and cost-effective gene therapy will require an in vivo approach in which the viral vector, or cells producing the viral vector, are directly administered to the patient in the form of an injection or simple implantation of RV producing cells.

This kind of in vivo approach, of course, introduces a variety of new problems. First of all, and above all, safety considerations have to be addressed. Virus will be produced, possibly from an implantation of virus producing cells, and there will be no opportunity to precheck the produced virus. It is important to be aware of the finite risk involved in the use of such systems, as well as trying to produce new systems that minimize this risk.

A further consideration for practical in vivo gene therapy, both from safety considerations as well as from an efficiency and from a purely practical point of view, is the targeting of RVs. It is clear that therapeutic genes carried by vectors should not be indiscriminately expressed in all tissues and cells, but rather only in the requisite target cell. This is especially important if the genes to be transferred are toxin genes aimed at ablating specific tumour cells. Ablation of other, nontarget cells would obviously be very undesirable.

The ability to target the delivery of genes to predefined cell types is presently difficult, regardless of the method used for gene transfer. The infection spectrum of enveloped viruses is determined by the interaction between viral surface (SU) proteins encoded by the retroviral gene, env, and host cell membrane proteins which act as receptors. Vectors derived from viruses will deliver genes to the same cell types as the original virus does, unless the infection spectrum of the vector virus is modified.

It has long been known that concurrent productive infection of cells with two types of enveloped virus can potentially lead to the production of mixed viral particles or "pseudotypes". These naturally produced "pseudotyped" viral particles may carry the core and genetic information of one virus, and in addition the surface proteins of the other virus (Weiss, R. A., In: *The Retroviridae*, 2:1–108, ed. J. A. Levy, Plenum Press, New York (1993)).

The most commonly used retroviral vectors (RVs) are derived from murine leukemia virus (MLV); a retrovirus that is able to infect many different cell types. This is due to the expression of the cognate receptor or recognition site, i.e. the cationic amino acid transporter for rodent cells (ecotropic virus) (Kim, J. W. et. al., *Nature*, 352:725–728 (1991); Wang, H. et. al., *Nature*, 352:729–731 (1991)) or the phosphate transporter/symporter (Miller, D. G. and Miller, D. A., *J. Virol.*, 68:8270–8276 (1994); van Zeijl, M. et. al., *Proc. Natl. Acad. Sci. USA*, 91:1168–1172 (1994)), for this virus on the surface of many different cell types. MLV has been the retrovirus of choice for the production of RVs, because of the capability of this virus to produce high titre systems, together with the fact that the MLV is a fairly simple virus, and that its biology is well understood. Other retroviruses or enveloped viruses are less promiscuous than MLV in their infection spectrum, but also often give rise to lower titre systems. It is also, at least presently, difficult to construct vectors based upon these virus systems, in part due to the complex nature of their life cycles (Günzburg, W. H. and Salmons, B., *Biochem. J.*, 283:625–632 (1992)).

One way, at least in theory, to combine the ability of viruses to target particular cell types at the level of infection is to create pseudotyped vector systems consisting of the core and genome of well established MLV based RV systems and the envelope of a second retrovirus or other enveloped virus that shows a limited infection spectrum. Such pseudotyped viruses would have an altered infection spectrum, since they are able to infect the same cells as the second virus providing the envelope and/or surface proteins.

Certain pseudotyped RVs have already been produced in the laboratory by a number of groups using packaging cell lines that produce gag and pol proteins from one virus and env proteins from a second virus.

For example, nontargeted, pseudotyped RVs based upon MLV and carrying the envelope protein of highly promiscuous vesicular stomatis virus (VSV) have been described (Yee, J. K. et. al., *Proc. Natl. Acad. Sci. USA*, 91:9564–9568 (1994)). These vectors give titres higher than $10^9$ (cf $10^6$ for MLV based RVs) and are more stable, facilitating their concentration. These MLV/VSV pseudotyped RVs show a very wide infection spectrum and are able to infect even fish cells. This suggests, that if such vectors were used for gene therapy they would be capable of infecting many non-target cells, which is very undesirable, especially if the vector is carrying a gene encoding a toxic gene product, for example to treat cancer.

Pseudotyped retroviral vectors based upon MoMuLV (MLV) and carrying the envelope of gibbon ape Leukemia virus (GaLV SEATO-MoMuLV hybrid virion) or the HTLV-I envelope protein (HTLV-I MoMuLV hybrid virion) have been described (Wilson, C. et. al., *J. of Virology*, 63(5):2374–2378 (1989)). The GaLV SEATO-MoMuLV hybrid particles were generated at titers approximately equivalent to those obtained with the MoMuLV particles, and the infection spectrum correlates exactly with the previously reported in vitro host range of wild type GaLV SEATO, i.e., bat, mink, bovine and human cells.

The apparent titers of HTLV-I MoMuLV (1–10 CFU/ml) were substantially lower than the titers achieved with either the MoMuLV or GaLV-MoMuLV recombinant virions. The HTLV-I hybrid virions were able to infect human and mink cells (Wilson, C. et. al., *J. of Virology*, 63(5):2374–2378 (1989)).

OBJECT OF THE INVENTION

The present invention relates to retroviral particles carrying the envelopes of heterologous viruses that are discriminating in their binding to host cell membrane bound receptors.

It is an object of the present invention to provide pseudotyped retroviral particles based upon MLV (Mouse Leukemia Virus) and the envelope of MMTV (Mouse Mammary Tumour Virus) which will deliver genes of interest to cell types as predefined by the tropism of the MMTV virus envelope, especially mammary epithelial cells and B-lymphocytes.

Such pseudotyped retroviral particles carrying therapeutic genes will be useful in the treatment of various retroviral infections and cancers, e.g. mammary cancer.

SUMMARY OF THE INVENTION

The invention then, inter alia, comprises the following, alone or in combination:

A retroviral vector system comprising a packaging cell line that synthesizes the core and enzymatic proteins of MLV from one or more gag and pol containing constructs and the envelope of a MMTV from the same or an independent env containing construct;

a retroviral vector system as above wherein the sequence encoding the TM domain of said env containing construct has been replaced by a sequence which codes for the TM domain of MLV;

a retroviral vector system as above wherein the cell line is selected from rodent, human, feline or mink cells;

a retroviral vector system as above wherein the gag, pol and env containing constructs are plasmids;

a retroviral vector system as above wherein the gag, pol and env are expressed from a promoter selected from the group of SV40, CMV, RSV, MLV or a house keeping promoter from a cellular gene;

a retroviral vector system as above wherein the plasmids are pRSVenv and pgagpolgpt;

a retroviral vector system as above which is transfected with a MLV based retroviral vector;

a retroviral vector system as above wherein the MLV based retroviral vector is a pBAG, or pLXSN based retroviral vector;

a retroviral vector system as above wherein the MLV based retroviral vector comprises, in operable linkage, a 5'LTR region originating from MLV and of the structure U3-R-U5; the ψ-region originating from MLV; one or more sequences selected from coding and non-coding sequences; and a 3'LTR region originating from MLV and of the structure U3-R-U5;

a retroviral vector system as above wherein the MLV based retroviral vector comprises, in operable linkage, a 5'LTR region originating from MLV and of the structure U3-R-U5; the ψ-region originating from MLV; one or more sequences selected from coding and non-coding sequences; and a 3LTR region originating from MLV and comprising a completely or partially deleted U3 region wherein said deleted U3 region is replaced by a polylinker sequence, followed by the R and U5 region;

a retroviral vector system as above, wherein said polylinker sequence carries at least one unique restriction site;

a retroviral vector system as above, wherein said polylinker sequence contains at least one insertion of a heterologous DNA fragment;

a retroviral vector system as above, wherein said heterologous DNA fragment is selected from one or more elements of the group consisting of regulatory elements and promoters;

a retroviral vector system as above wherein said coding sequences comprises additionally at least one non coding sequence selected from regulatory elements and promoters;

a retroviral vector system as above, wherein said regulatory elements and promoters are target cell specific in their expression;

a recombinant vector as above, wherein said target cell specific regulatory elements and promoters are selected from one or more elements of the group consisting of HIV, WAP, MMTV, β-lactoglobulin and casein specific regulatory elements and promoters, pancreas specific regulatory elements and promoters including carbonic anhydrase II and β-glucokinase regulatory elements and promoters, lymphocyte specific regulatory elements and promoters including immunoglobulin and MMTV lymphocytic specific regulatory elements and promoters and MMTV specific regulatory elements and promoters such as $^{MMTV}P_2$ conferring responsiveness to glucocorticoid hormones or directing expression to the mammary gland, T-cell specific regulatory elements and promoters such as the T-cell receptor gene, the CD4 receptor promoter, and B-cell specific regulatory elements and promoters such as the immunoglobulin promoter and mb1;

a retroviral vector system as above, wherein said regulatory elements and promoters regulate the expression of at least one of the coding sequences of said MLV based retroviral vector;

a retroviral vector system as above, wherein said coding sequence is selected from one or more elements of the group consisting of marker genes, therapeutic genes, antiviral genes, antitumour genes, cytokine genes;

a retroviral vector system as above, wherein said marker or therapeutic gene is selected from the group consisting of marker genes which codes for proteins such as β-galactosidase, neomycin, alcohol dehydrogenase, puromycin, hypoxanthine phosphoribosyl transferase (HPRT), hygromycin and secreted alkaline phosphatase or therapeutic genes which codes for proteins such as Herpes Simplex Virus thymidine kinase, cytosine deaminase, guanine phosphoribosyl transferase (gpt), cytochrome P450 and cell cycle regulatory genes which codes for proteins such as SDI or tumor suppressor genes which codes for proteins such as p53 or antiproliferation genes which codes for proteins such as melittin, cecropin or cytokines such as IL-2;

a retroviral vector system as above, wherein the retroviral sequences involved in integration of the MLV based vector are altered or at least partially deleted;

a retroviral vector system as above, wherein said MLV based vector carries a DNA fragment which is homologous to one or more cellular sequences or a part thereof;

a retroviral vector system as above, wherein said regulatory elements are regulatable by transacting molecules;

use of a retroviral vector system as above for production of pseudotyped retroviral particles;

a pseudotyped retroviral particle produced by culturing a retroviral vector system as above followed by isolation of the retroviral particle;

pharmaceutical composition comprising a pseudotyped retroviral particle as above;

pharmaceutical composition comprising a retroviral vector system as above;

a non-therapeutical or therapeutical method for introducing heterologous and/or homolgous DNA into human or animal cells susceptible to infection by MMTV viruses in vitro or in vivo comprising infecting a cell population with a retroviral particle as above; and a host cell infected with a retroviral particle as above.

DETAILED DESCRIPTION OF THE INVENTION

Figure 1:
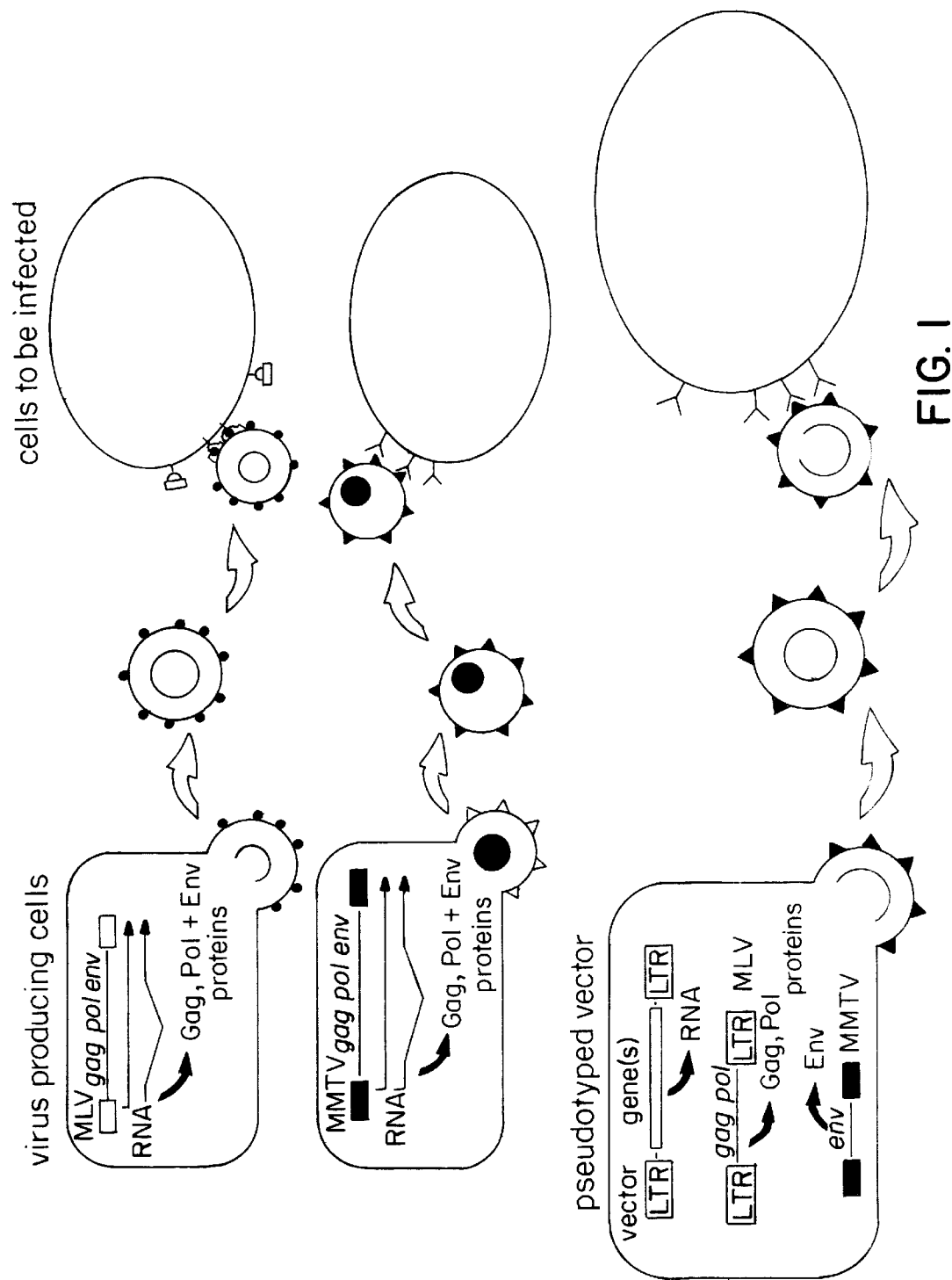
FIG. 1 is a schematic showing virus producing cells and cells to be infected.

Retroviral Vector Systems Consist Of Two Components:

1) the retroviral vector itself is a modified retrovirus (vector plasmid) in which the genes encoding for the viral proteins have been replaced by therapeutic genes optionally including marker genes to be transferred to the target cell. Since the replacement of the genes encoding for the viral proteins effectively cripples the virus it must be rescued by the second component in the system which provides the missing viral proteins to the modified retrovirus.

The second component is:

2) a cell line that produces large quantities of the viral proteins, however lacks the ability to produce replication competent virus. This cell line is known as the packaging cell line and consists of a cell line transfected with a second plasmid carrying the genes enabling the modified retroviral vector to be packaged. This plasmid directs the synthesis of the necessary viral proteins required for virion production.

To generate the packaged vector, the vector plasmid is transfected into the packaging cell line. Under these conditions the modified retroviral genome including the inserted therapeutic and optional marker genes is transcribed from the vector plasmid and packaged into the modified retroviral particles (recombinant viral particles). A cell infected with such a recombinant viral particle cannot produce new vector virus since no viral proteins are present in these cells. However the vector carrying the therapeutic and marker genes is present and these can now be expressed in the infected cell, and in all daughter cells.

The inventors of the present invention have established a retroviral vector system comprising packaging cell lines that synthesize the core and enzymatic proteins of MLV from at least one gag and pol containing construct and the envelope of MMTV from the same or an independent env containing construct.

The present invention thus relates to targeted pseudotyping comprising the use of the env from a virus that exhibit a narrow, well defined and specific infection spectrum, namely MMTV.

In summary the approach disclosed in the present patent application results in the targeted delivery of genes to cell types that can be infected by MMTV virus, i.e. mammary epithelial cells and B-lymphocytes.

The envelope gene of retroviruses encodes two proteins, one of which is a transmembrane protein (TM) which spans the host cell membrane and is involved in the interaction between the envelope and the core of the virus; as well as a second protein which is a surface protein (SU) which is involved in the interaction between the virus particle and the host cell during the initiation of the infection event through its anchor to the TM. It is possible to retain either the MLV TM or the TM domain that interacts with the core of MLV, while replacing the SU, or the SU and the TM domain that interacts with the SU to obtain a packaging cell line which will produce another type of pseudotyped viral particles comprising chimeric envelope proteins.

In another embodiment, the invention thus comprises a retroviral vector system as above wherein the sequence encoding the TM domain of said env containing construct has been replaced by a sequence which codes for the TM domains of MLV virus.

In a further embodiment, the invention comprises a retroviral vector system consisting of a packaging cell line that synthesizes the core and enzymatic proteins of MLV from at least one gag and pol containing construct and the envelope of MMTV from the same or an independent env containing construct, which is transfected with a MLV based retroviral vector.

The MLV based retroviral vector comprises, in operable linkage, at least the 5'LTR region originating from MLV; one or more sequences selected from coding and non-coding sequences; and the 3'LTR region originating from MLV.

The MLV based vector is preferably selected from pBAG (Price, J. et. al., *Proc. Natl. Acad. Sci USA*, 84:156–160 (1987)) or pLXSN (Miller, A. D. and Rosmann, G. J., *BioTechniques*, 7:980–990 (1989)) based vectors.

Promoter Conversion vectors:

The retroviral genome consists of an RNA molecule with the structure R-U5-gag-pol-env-U3-R. During the process of reverse transcription, the U5 region is duplicated and placed at the right hand end of the generated DNA molecule, whilst the U3 region is duplicated and placed at the left hand end of the generated DNA molecule. The resulting structure U3-R-U5 is called LTR (Long Terminal Repeat) and is thus identical and repeated at both ends of the DNA structure or provirus. The U3 region at the left hand end of the provirus harbours the promoter (see below). This promoter drives the synthesis of an RNA transcript initiating at the boundary between the left hand U3 and R regions and terminating at the boundary between the right hand R and U5 region. This RNA is packaged into retroviral particles and transported into the target cell to be infected. In the target cell the RNA genome is again reverse transcribed as described above.

According to the ProCon principle a retroviral vector can be constructed in which the righthand U3 region is altered, but the normal left hand U3 structure is maintained; the vector can be normally transcribed into RNA utilizing the normal retroviral promoter located within the left hand U3 region. However the generated RNA will only contain the altered right hand U3 structure. In the infected target cell, after reverse transcription, this altered U3 structure will be placed at both ends of the retroviral structure.

If the altered region carries a polylinker instead of the U3 region then any promoter, including those directing tissue specific expression (see below) can be easily inserted. This promoter will then be utilized exclusively in the target cell for expression of linked genes carried by the retroviral vector. Alternatively or additionally DNA segments homologous to one or more cellular sequences can be inserted into the polylinker for the purposes of gene targeting.

In the packaging cell line the expression of the retroviral vector is regulated by the normal unselective retroviral promoter. However as soon as the vector enters the target cell promoter conversion occurs, and the therapeutic genes are expressed from a tissue specific promoter of choice introduced into the polylinker. Not only can virtually any tissue specific promoter be included in the system, providing for the selective targeting of a wide variety of different cell types, but additionally, following the conversion event, the structure and properties of the retroviral vector no longer resembles that of a virus. This, of course, has extremely important consequences from a safety point of view, since ordinary or state of the art retroviral vectors readily undergo genetic recombination with the packaging vector to produce potentially pathogenic viruses. Promoter conversion (Procon) vectors do not resemble retroviruses because they no longer carry U3 retroviral promoters after conversion thus reducing the possibility of genetic recombination.

For a complete disclosure of the ProCon vectors, the content of International application No. PCT/EP95/03445 is completely included within the present application or incorporated herein by reference.

In a further embodiment, the invention the MLV based vector thus comprises, in operable linkage, a 5'LTR region originating from MLV and of the structure U3-R-U5; the ψ-region of MLV; one or more sequences selected from coding and non-coding sequences; and a 3'LTR region originating from MLV and comprising a completely or partially deleted U3 region wherein said deleted U3 region is replaced by a polylinker sequence, followed by the R and U5 region.

With reference to the ProCon vectors, said polylinker sequence carries at least one unique restriction site and contains preferably at least one insertion of a heterologous DNA fragment. Said heterolgous DNA fragment is preferably selected from regulatory elements and promoters, preferably being target cell specific in their expression.

Gene expression is regulated by promoters. In the absence of promoter function a gene will not be expressed. The normal MLV retroviral promoter is fairly unselective in that it is active in most cell types. However a number of promoters exist that show activity only in very specific cell types. Such tissue-specific or inducible promoters will be the ideal candidates for the regulation of gene expression in retroviral vectors, limiting expression of the therapeutic genes to specific target cells.

The target cell specific regulatory elements and promoters are preferably selected from, but not limited to, one or more elements of the group consisting of HIV, Whey Acidic Protein (WAP), Mouse Mammary Tumour Virus (MMTV), β-lactoglobulin and casein specific regulatory elements and promoters, which may be used to target human mammary tumours, pancreas specific regulatory elements and promoters including carbonic anhydrase II and β-glucokinase regulatory elements and promoters, lymphocyte specific regulatory elements and promoters including immunoglobulin and MMTV lymphocytic specific regulatory elements and promoters and MMTV specific regulatory elements and promoters conferring responsiveness to glucocorticoid hormones or directing expression to the mammary gland, T-cell specific regulatory elements and promoters such as from the T-cell receptor gene and CD4 receptor promoter and B-cell specific regulatory elements and promoters such as immunoglobulin promoter or mb1. Said regulatory elements and promoters regulate preferably the expression of at least one of the coding sequences of said retroviral vector.

Another promoter is the HIV promoter or a minimal promoter placed under the regulation of the HIV tat responsive element (TAR) to target HIV infected cells. Targeting will be achieved because the HIV promoter is dependent upon the presence of Tat, an HIV encoded autoregulatory protein (Haseltine, W. A., FASEB J. 5:2349–2360 (1991)).

Thus only cells infected with HIV and therefore expressing Tat will be able to produce the peptide encoded by the vector. Alternatively, the peptide could be expressed from T-cell specific promoters such as that from the CD4 or T-cell receptor gene. In order to target tumour cells, promoters from genes known to be overexpressed in these cells (for example c-myc, c-fos) may be used.

Peptide encoding sequences may be placed also under the transcriptional control of other promoters known in the art. Examples for such promoters are of the group of SV40, cytomegalovirus, Rous sarcoma virus, β-actin, HIV-LTR, MMTV-LTR, B or T-cell specific and tumour specific promoters.

In one embodiment of the invention the encoded peptide is expressed from MMTV promoters such as the $^{MMTV}$P2 promoter (Günzburg, W. H., et. al., Nature 364:154–158 (1993)).

According to a preferred embodiment of the invention at least one retroviral sequence encoding for a retroviral protein involved in integration of retroviruses is altered or at least partially deleted.

The vector preferably contains DNA fragments homologous to one or more cellular sequences.

The regulatory elements and promoters are preferably regulatable by transacting molecules.

According to the invention the term "polylinker" is used for a short stretch of artificially synthesized DNA which carries a number of unique restriction sites allowing the easy insertion of any promoter or DNA segment. The term "heterologous" is used for any combination of DNA sequences that is not normally found intimately associated in nature.

A retroviral vector refers to a DNA sequence retroviral vector on the DNA sequence level.

The retroviral vector system and the pseudotyped retroviral particle according to the invention may be used for producing a pharmaceutical composition for somatic gene therapy in mammals including humans. Furthermore, they can be used for targeted integration in homologous cellular sequences.

The retroviral promoter structure is termed LTR. LTR's carry signals that allow them to integrate into the genome of the target cell. Such integrating elements can also contribute to pathogenic changes. Retroviral vectors can carry modified LTRs that no longer carry the signals required for integration. Again this increases the potential safety of these vector systems.

The pseudotyped retroviral particles according to the invention can suitably be administered in the form of an injection or by implantation of the retroviral vector system according to the invention, suitably as encapsulated cells producing the pseudotyped retroviral particles according to the invention (see Danish patent application NO. 740/95).

Figure 2:
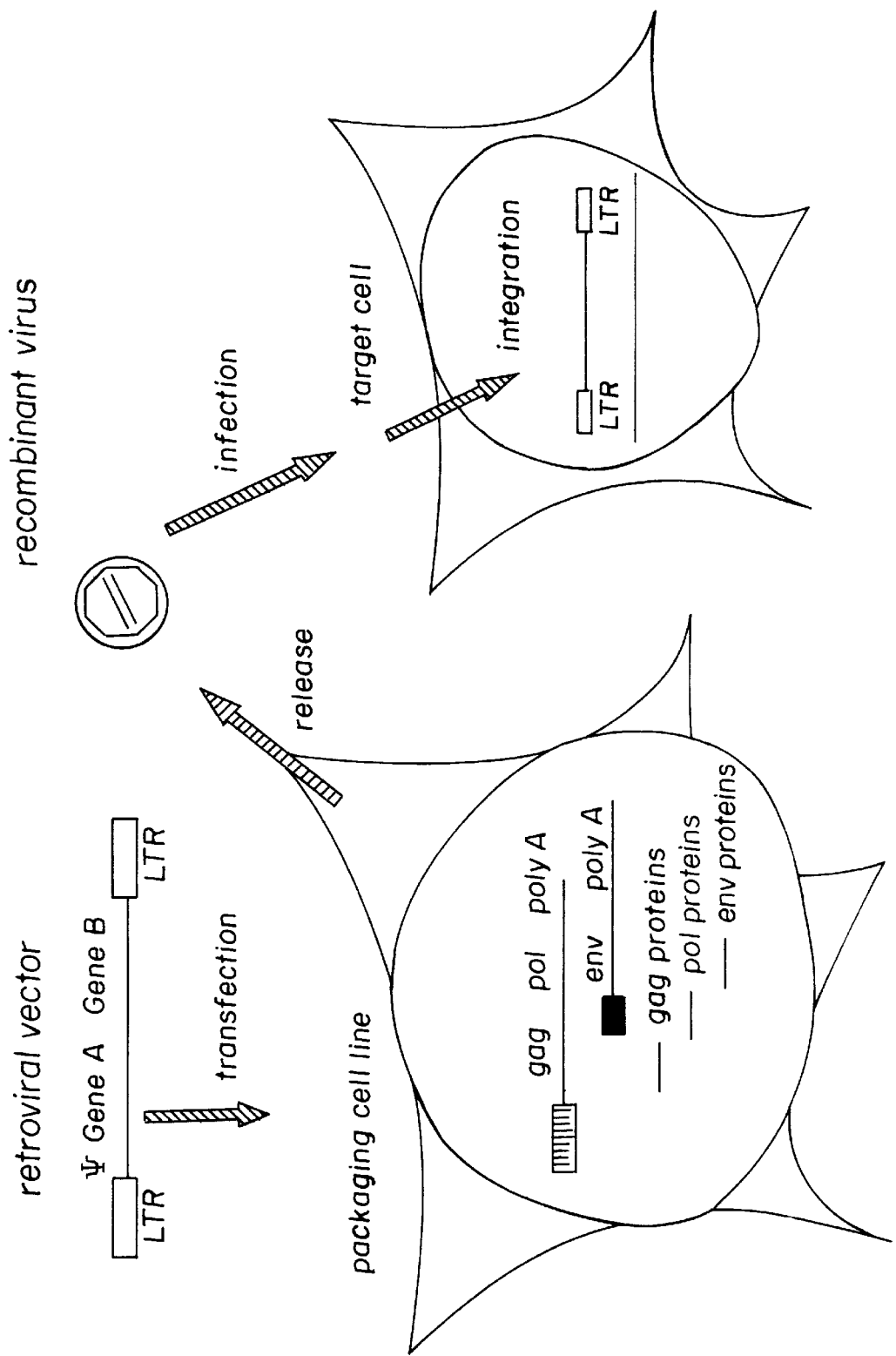
FIG. 2 is a schematic of a retroviral vector of the present invention.

The following examples describe a pseudotyped vector, but it will be well understood by a person skilled in the art, that the provided examples in no way may be interpreted in a way that limits the applicability of the technology provided by the present invention to these vectors. According to the present invention a pseudotyped retroviral vector based upon MLV and Mouse Mammary Tumour Virus (MMTV), a retrovirus that seems to preferentially infect mammary epithelial cells and B-lymphocytes (Günzburg, W. H. & Salmons, B. Biochem. J. 283:625–632 (1992)), have been constructed. This system consists of a packaging cell line, based upon a cell line that is able to process the relevant viral proteins, that has been modified to carry two individual genes (FIGS. 1 and 2). One of these constructs can express the MLV core proteins (gag) and enzymatic functions (pol) from any strong promoter (in the case of this example, the MLV promoter). The second construct expresses the MMTV envelope proteins also from a strong promoter (e.g. that of Rous sarcoma virus).

EXAMPLE

The expression construct for the MMTV envelope (env) proteins was cloned by restriction digest of plasmid carrying the complete MMTV genome, pGR102 (Salmons, B., et. al.

*Virology* 101–114 (1985)), with AatII and HindIII. The obtained fragment (4.1 kb) carrying the entire env region and the 3' LTR of MMTV was ligated into pRSV-2 (a gift from C. Gorman) digested with AatII and HindIII and resulted in the plasmid pRSVenv. The MMTV env region is now under transcriptional control of the RSV promoter, the polyadenylation signal is located in the MMTV 3' LTR. A plasmid carrying the gag-pol region of MLV as well as a selectable marker gene (gpt) was obtained from Arthur Bank (Markowitz, D., et. al. *J. Virol.* 62:1120–1124 (1988a)); (Markowitz, D., et. al. *Virology,* 167,400–406 (1988b)). Both plasmids were co-transfected into one of the few cell lines permissive for MMTV, CK ((Salmons, B., et. al. *Virology* 101–114 (1985)), and cell clones were isolated and shown to carry each construct. These cells were transfected with pBAG, a MLV based retroviral vector carrying a gene conferring antibiotic resistance as well as a β-galactosidase indicator gene (Price, J. et. al., *Proc. Natl. Acad. Sci. USA* 84:156–160 (1987)). The resultant virus was used to infect CK cells which are permissive for MMTV but not ecotropic MLV infection. G418 antibiotic resistant and thus infected clones were only obtained with pseudotyped vector and not with vector obtained from an MLV ecotropic (eco) packaging cell line (Markowitz, D. et. al. *J. Virol.* 62:1120–1124 (1988a)), as expected (Table I). As a control virus from an MLV packaging cell line, producing virus particles with a wide, nontargeted expression spectrum (Markowitz, D., et. al. *Virology,* 167,400–406 (1988b)), was also able to infect CK cells (MLV ampho; Table I). Cell clones infected with the pseudotyped vector could also be shown to express the β-galactosidase indicator gene.

TABLE I

Titre of virus production from different packaging cell lines on MMTV permissive CK, XC and ML cells

| Packaging cell line | Vector | Target Cells | G418 cols/ml resistant |
|---|---|---|---|
| MLV packaging system | | | |
| NIH/3T3: Psi-2, GP + E86 (MLV eco) | BAG | CK | 0 |
| NIH/3T3: pa 317 (MLV ampho) | BAG | CK | ~800 |
| Pseudotype packaging system | | | |
| CK: MLV gag/pol and MMTV env | BAG | CK | ~50 |
| CK: MLV gag/pol and MMTV env | LXSN | XC | 200 |
| CK: MLV gag/pol and MMTV env | LXSN | ML | 8000 |

Cell lines in bold formed the basis for the packaging cells.

The following abbreviations are used in the description of the invention:

| ampho means: | amphotropic |
|---|---|
| "CD" means: | Cluster of Differentiation |
| "CK" means: | Cat Kidney cells |
| "XC" means: | Rat fibrosarcoma cell line |
| "ML" means: | Mink lung epithelial cell line |
| "NIH3T3" means: | Mouse fibroblast cells |
| "eco" means: | ecotropic |
| "env" means: | "envelope" gene region |
| "gag" means: | "group specific antigen" gene region |
| "gpt" means: | "Xanthine-Guanine-Phosphoribosyl-Transferase |

-continued

| "HIV" means: | Human Immunodeficiency Virus |
|---|---|
| "HTLV" means: | Human T-cell Lymphotropic Virus (Human T-cell leukemia virus) |
| "LTR" means: | Long Terminal Repeat |
| "MLV" means: | Murine Leukemia Virus (MoMuLV) |
| "MMTV" means: | Mouse Mammary Tumour Virus |
| "pol" means: | "polymerase" gene region |
| "RSV" means: | Rous Sarcoma Virus |
| "RV" means: | Retroviral Vector |
| "SIV" means: | Simian Immunodeficiency Virus |
| "SU" means: | Surface protein |
| "TM" means: | Transmembrane protein |
| "VSV" means: | Vesicular Stomatis Virus |
| "eco" means: | ecotropic |
| "CMV" means: | cytomegalovirus |

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A packaging cell line comprising the core and enzymatic proteins of murine leukemia virus synthesized from one or more gag and pol containing constructs and the envelope (env) of mouse mammary tumour virus synthesized from the same or an independent env containing construct.

2. The packaging cell line according to claim 1 wherein the sequence encoding the transmembrane protein domain of said env containing construct has been replaced by a sequence which codes for the transmembrane protein domain of murine leukemia virus.

3. The packaging cell line according to claim 1 wherein the cell line is selected from the group consisting of rodent cells, human cells, feline cells and mink cells.

4. The packaging cell line according to claim 1 wherein the gag-, pol- and env-sequences are expressed from a promoter selected from the group consisting of SV40, cytomegalovirus, rous sarcoma virus, murine leukemia virus and a house keeping promoter from a cellular gene.

5. The packaging cell line according to claim 1 which is transfected with a murine leukemia virus based retroviral vector.

6. The packaging cell line according to claim 5 wherein the murine leukemia virus based retroviral vector comprises, in operable linkage:
a) a 5'LTR region originating from murine leukemia virus and of the structure U3-R-U5;
b) the ψ-region originating from murine leukemia virus;
c) one or more sequences selected from coding and non-coding sequences; and
d) a 3'LTR region originating from murine leukemia virus and comprising a completely or partially deleted U3 region wherein said deleted U3 region is replaced by a polylinker sequence carrying at least one unique restriction site, followed by the R and U5 region.

7. The packaging cell line according to claim 6 wherein one or more heterologous DNA fragments are inserted into said polylinker sequence.

8. A packaging cell line according to claim 7, wherein said heterologous DNA fragment is selected from one or more elements of the group consisting of regulatory elements and promoters, regulatory elements and promoters that are target cell specific in their activity and regulatory elements that are regulatable by transacting molecules.

9. A packaging cell line according to claim 6, wherein said coding sequence comprises additionally at least one non coding sequence selected from the group consisting of regulator elements and promoters, regulatory elements and promoters that are target cell specific in their activity and regulatory elements that are regulatable by transacting molecules, said non coding sequences regulating the expression of at least one of the coding sequences of said retroviral vector.

10. A packaging cell line according to claim 6, wherein at least one of said coding sequence is selected from one or more elements of the group consisting of marker genes, therapeutic genes, antiviral genes, antitumour genes, cytokine genes.

11. A method for introducing DNA into a human or animal cell susceptible to infection by mouse mammary tumour virus in vitro comprising infecting the human or animal cell with a retroviral particle produced by the packaging cell line according to claim 10.

12. The pseudotyped retroviral particle produced by the packaging cell line according to claim 6.

13. A method for introducing the coding and noncoding sequences present in the retroviral vector of claim 12 into a human or animal cell susceptible to infection by mouse mammary tumour virus in vitro comprising infecting the human or animal cell with the pseudotyped retroviral particle according to claim 12.

14. A method of producing pseudotyped retroviral particles which include a retroviral vector, comprising transfecting the packaging cell line of claim 1 with the retroviral vector under conditions in which the retroviral vector is inserted into the genome of the packaging cell line thereby producing a packaging cell line characterized by a modified genome, wherein upon transcription of the modified genome, pseudotyped retroviral particles which include the retroviral vector are produced.

15. The method of claim 14 wherein the packaging cell line is transfected with a murine leukemia virus based retroviral vector.

16. The pseudotyped retroviral particle produced by the packaging cell line according to claim 1.

17. A host cell infected with a retroviral particle according to claim 16.

18. A method for introducing DNA into a human or animal cell susceptible to infection by mouse mammary tumour virus in vitro comprising transfecting the packaging cell line of claim 1 with a retroviral vector comprising the DNA under conditions in which the retroviral vector is inserted into the genome of the packaging cell line thereby producing a packaging cell line characterized by a modified genome, wherein upon transcription of the modified genome, pseudotyped retroviral particles which include the retroviral vector are produced; infecting the human or animal cell with the pseudotyped retroviral particles, thereby introducing the DNA into the human or animal cell.

* * * * *